United States Patent
Traxel et al.

(10) Patent No.: US 6,332,780 B1
(45) Date of Patent: Dec. 25, 2001

(54) IMPLANT SIMULATING DEVICE

(75) Inventors: Doris Traxel, Basel; Urs Weber, Reigoldswil, both of (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/573,571

(22) Filed: May 19, 2000

Related U.S. Application Data

(63) Continuation-in-part of application No. PCT/CH97/00440, filed on Nov. 21, 1997.

(51) Int. Cl.$^7$ .................................................. G09B 23/28
(52) U.S. Cl. .............................. 434/267; 434/274; 606/61
(58) Field of Search ................................... 434/267, 274, 434/275; 606/60, 61; 425/2

(56) References Cited

U.S. PATENT DOCUMENTS

| | | | |
|---|---|---|---|
| 5,152,303 | * 10/1992 | Allen | 128/898 |
| 5,154,718 | * 10/1992 | Cozad et al. | 606/61 |
| 5,658,286 | 8/1997 | Sava | 606/61 |

FOREIGN PATENT DOCUMENTS 2 267 757 A   12/1993   (GB) .

* cited by examiner

*Primary Examiner*—Kien T. Nguyen
(74) *Attorney, Agent, or Firm*—Pennie & Edmonds LLP

(57) ABSTRACT

The present invention relates to a device and method for simulating the position and orientation of fixation elements that form part of a fixation system. By simulating the position and orientation of the fixation elements, the shape of the load carrier used for connecting the fixation elements can be determined. Making this determination prior to implantation of the load carrier is particularly useful for minimally invasive procedures in which the entire operative field is not directly visible. The device includes a base plate with two arms having tracks and crossbars which are capable of displacement in the plane of the base plate and which can be fixed in any position using tightening screws. The crossbars include integrated ball joints into which fixation element simulators can be screwed together with the same inserters as used for the implanted fixation elements so that the height of the fixation element simulators can be adjusted. The device also includes a correlation system for positioning the fixation element simulators in the device so that they have the same position and orientation relative to each other as the implanted fixation elements.

17 Claims, 6 Drawing Sheets

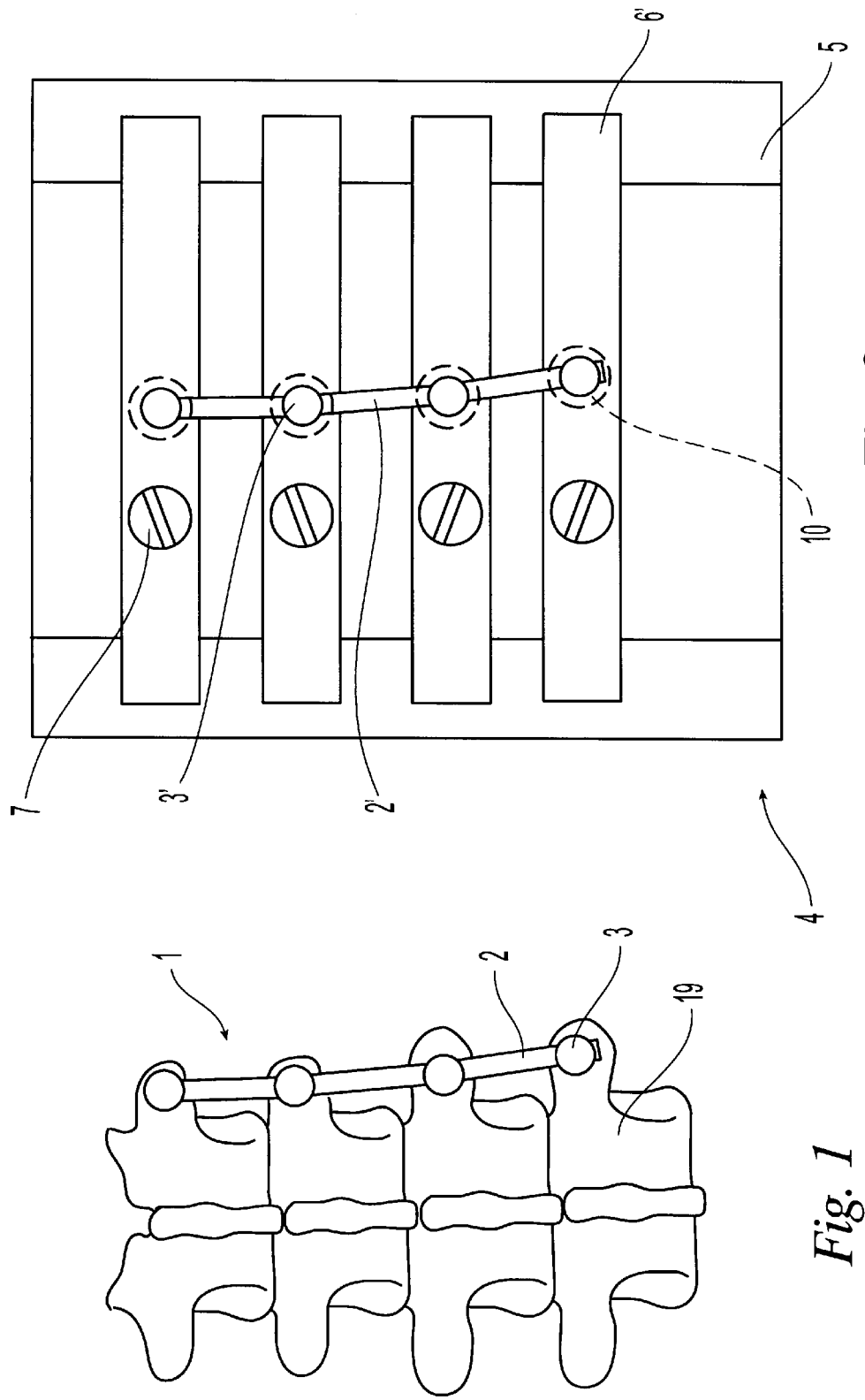

IMPLANT SIMULATING DEVICE

CROSS-REFERENCE TO RELATED APPLICATIONS

This application is a continuation-in-part of the U.S. National Stage designation of co-pending International Patent Application PCT/CH97/00440, filed Nov. 21, 1997, the entire content of which is expressly incorporated herein by reference thereto.

FIELD OF THE INVENTION

The present invention relates to a device for simulating the position and orientation of at least a portion of an implanted fixation system, so that, for example, a spinal fixation rod can be pre-bent for insertion in implanted pedicle screws and/or hooks using a minimally invasive surgical procedure rather than an open surgical procedure.

BACKGROUND OF THE INVENTION

It is often necessary to surgically treat spinal disorders such as scoliosis. Numerous systems have been used for spinal correction and fixation. These fixation systems are well known and usually include one or more elongated members, typically either rods or plates, placed along the vertebral column. The elongated member is attached to the spine typically with a plurality of various fasteners, which may include, but are not limited to, pedicle screws, plates, transverse process hooks, sublaminar hooks, pedicle hooks, and other similar devices.

The fasteners are typically implanted prior to their attachment to the elongated member, with the elongated member then being bent and/or cut to be received by the plurality of fasteners. By fashioning the elongated member to fit implanted fasteners, the overall fit of the fixation system is more likely to be proper than if the elongated member is attached to the plurality of fasteners, each fastener in turn then being attached to the spine. FIG. 1 illustrates one such prior art fixation system 1 affixed to a spine 19. Fixation system 1 includes a plurality of fasteners or fixation elements 3 connected by an elongated member or rod 2, which has been bent appropriately to fit the shape proscribed collectively by fixation elements 3.

In an open surgery procedure, the wide exposure of the spine and the surrounding anatomy simplifies contouring the elongated element to the fasteners. However, such exposure can result in significant damage to the soft tissue, particularly the muscles. This damage can lead to weakening in the muscular area, and thus to weakening in the retaining system for the spine or other extremities and also entails the risk of scarring, which, in turn, can lead to postoperative problems.

In an effort to avoid the possible complications associated with open surgical procedures, so-called minimally invasive procedures can be used for implantation of a fixation system. During such a procedure, several percutaneous incisions are made, leaving the posterior back muscles largely intact. The fasteners are then placed through the skin, preferably with the help of a computer assisted surgery system (CAS) such as that described, for example, in U.S. Pat. No. 5,383,454. The fasteners are typically inserted through the incisions using an inserter having a shaft of sufficient length so that the end projects through the skin. In such situations, the sensors or transmitters associated with the CAS can be located on either the end of the inserter or directly on the fastener.

Irrespective of whether a CAS is used during a minimally invasive implantation of a fixation system, contouring the elongated element is problematic because unlike an open surgical procedure, the fasteners are not directly visible and it has not been possible to use a trial rod or a bending template.

Thus, there exists a need for a device for simulating the position and orientation of at least a portion of an implanted fixation system, so that, for example, a spinal fixation rod can be pre-bent for insertion in implanted pedicle screws and/or hooks using a minimally invasive surgical procedure.

SUMMARY OF THE INVENTION

The present invention relates to a device for simulating position and orientation of an elongated element with respect to a plurality of fixation elements of a fixation system. The implant simulating device includes a base plate and first and second arms extending from the base plate. Each arm defines a track into which at least two cross members are slidingly engaged. Each cross member also has a locking element for fixing the position of the cross member. A fixation element simulator is associated with each of the cross members and is capable of angular positioning with respect to the cross members. The implant simulating device also includes a correlation system for correlating at least two fixation element simulators to at least two fixation elements of the fixation system. Coupling of an elongated element in the fixation element simulators after correlation by the correlating system allows the elongated element to be configured and dimensioned for coupling to the fixation elements prior to implantation.

Each cross member can include a ball joint for receiving and positioning one of the fixation element simulators. In one embodiment, each cross member comprises top and bottom bars and a center piece located therebetween, in which the ball joint is located. In this embodiment, each cross member is designed such that the ends of the bottom bar slide within the track of the first and second arms so that each cross member is slidable in a direction parallel to the length of the base plate and in a direction parallel to the width of the base plate. If the fixation element simulators have a threaded portion, each ball joint can have a threaded bore for engaging the threaded portion of the fixation element simulator to allow height adjustment of the fixation element simulator.

The cross members can be made to be flexible so that if the elongated element is bent further than the bend needed to contour the elongated element to the fixation element simulators, the cross members deform to simulate changes in anatomy. Advantageously, the elongated element may be used as trial rod or a template for bending a second elongated element that can then be coupled to the fixation elements.

In an exemplary embodiment, the correlation system is a position detecting system comprising at least one signal transmitter, at least one sensor for detecting the signal(s), and an analyzing unit for processing the signal(s) to determine position and orientation of at least some of the fixation elements. A signal transmitter can be associated with each fixation element, either located directly on the fixation element or located on an elongated inserter which is associated with a fixation element and is configured and dimensioned to mate with a fixation element simulator. The signal may be an electromagnetic or acoustic wave. For example, each signal transmitter can be at least one light emitting diode (LED) and the sensor is a digital camera.

In another embodiment, the correlation system uses a mechanical mechanism, such as a pantograph, a scanning device, or a combination thereof. For example, the correlation system can be a translation device for transferring position and orientation of at least some of the plurality of fixation elements. The translation device includes at least two translators and a connecting rod linking the at least two translators. Each of the translators has a positioning pin with first and second ends and a sleeve with first and second ends. The first end of the sleeve receives the first end of the positioning pin and the second end of the sleeve receives at least a portion of an elongated inserter coupled to a fixation element. Each translator also includes a clamp having a first portion coupled to the connecting rod and a second portion coupled to the second end of the positioning pin. The first portion of the clamp rotates with respect to the second portion for adjusting position and orientation of the positioning pin to align the translator with one of the plurality of fixation elements. Transferring each of the translators to one of the fixation element simulators results in the implant simulating device mimicking at least a portion of the fixation system.

The implant simulating device according to the present invention can also include an elongated element inserter for guiding implantation of the elongated element. The elongated element inserter has a handle and an elongated holder extending from the handle in a first direction and having a hollow shaft with a recess on a distal end for receiving a portion of the elongated element. A locking pin inserts in the hollow shaft of the holder for securing the longitudinal element in the recess. The elongated element inserter also includes a position and orientation display extending from the handle in a second direction and having a length scale. The position and orientation display is parallel to the portion of the elongated element and remain above the skin as the elongated element is implanted.

The present invention also relates to a method for prebending an elongated element prior to coupling to fixation elements that have been implanted using a minimally invasive procedure. An elongated inserter is mounted on each of at least two of the implanted fixation elements. The position and orientation of these fixation elements are transferred to at least two fixation element simulators to thereby mimic the desired shape (as defined collectively by the implanted fixation elements). The elongated element or some analog, e.g. a trial rod or bending template, is then bent to have a configuration that matches the desired shape.

BRIEF DESCRIPTION OF THE DRAWINGS

Preferred features of the present invention are disclosed in the accompanying drawings, wherein similar reference characters denote similar elements throughout the several views, and wherein:

FIG. 1 shows a top view of a portion a prior art fixation system usable with the implant simulating device according to the present invention.

FIG. 2 shows a top view of one embodiment of the implant simulating device according to the present invention.

DETAILED DESCRIPTION OF PREFERRED EMBODIMENTS

As shown in FIG. 2, an implant simulating device 4 according to the present invention includes an elongated element 2' and fixation element simulators 3' for simulating fixation elements 3. Preferably, fixation element simulators 3' are identical or substantially similar to the implanted fixation elements 3. Elongated element 2' can be either the actual implant that will be used in the patient, i.e. elongated element 2 shown in FIG. 1, or an analog to the actual element, e.g. a bending template or a trial rod.

Figure 3:
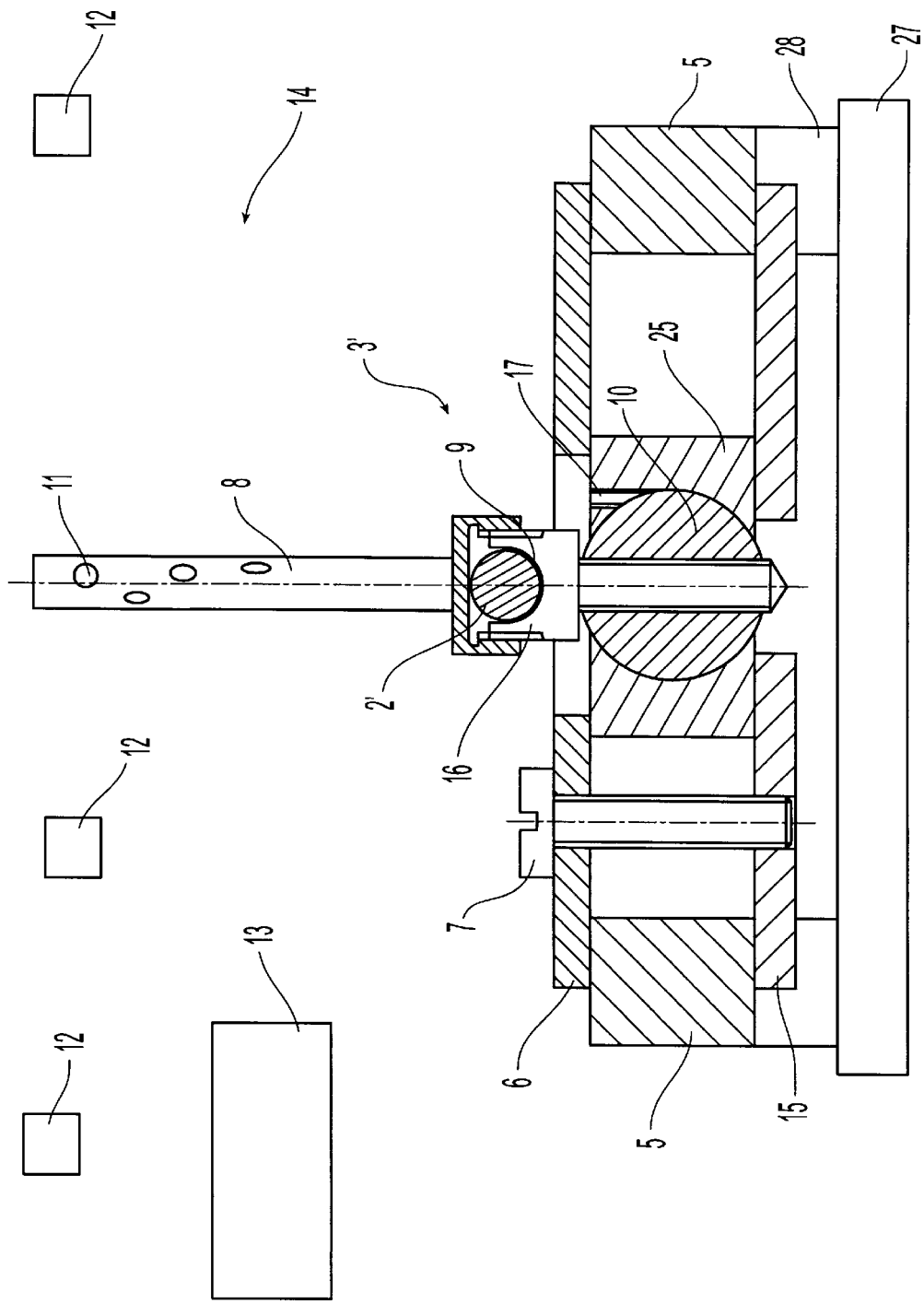
FIG. 3 shows a cross-sectional view of the implant simulating device of FIG. 2 with the position detecting system schematically shown.
Figure 4:
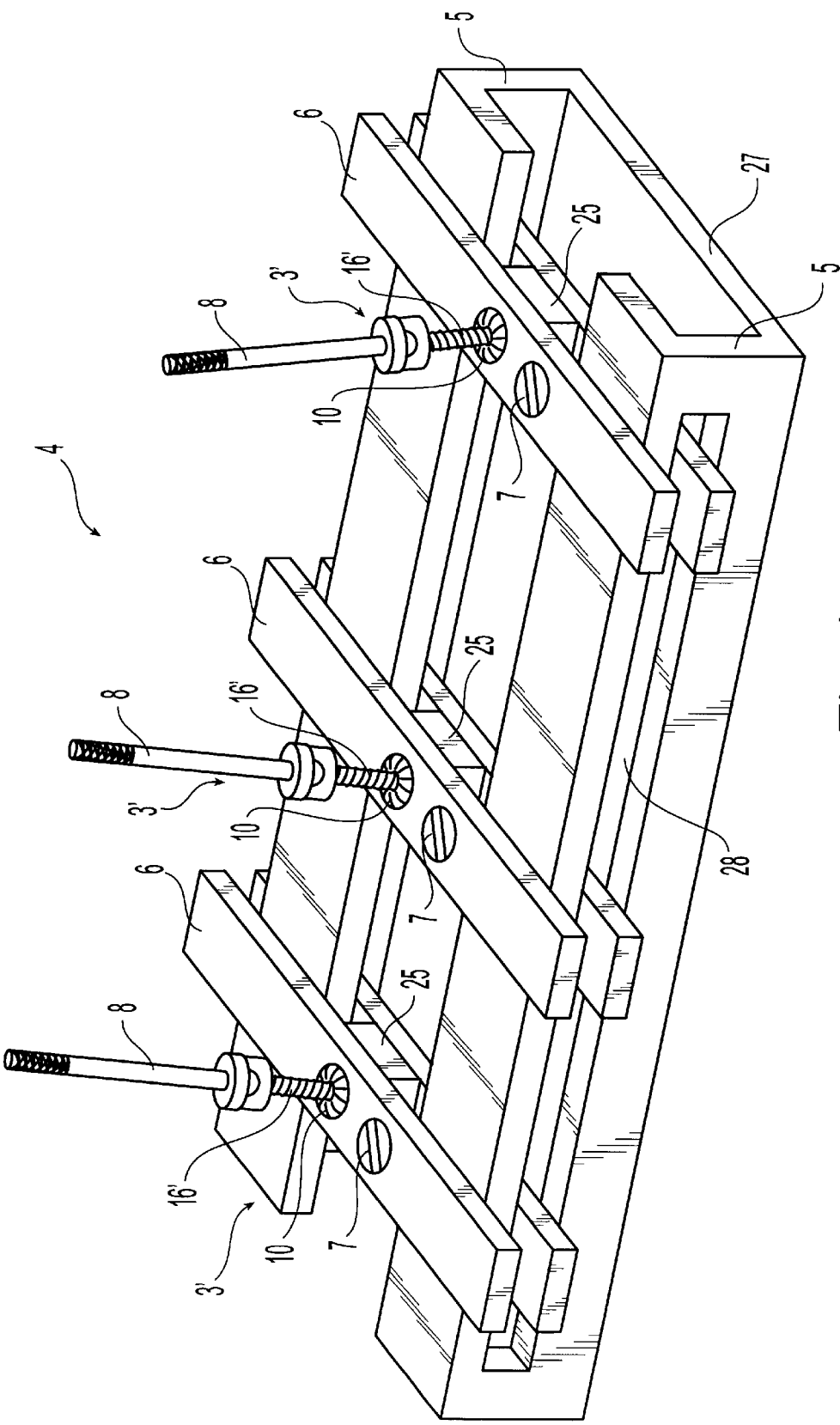
FIG. 4 shows a perspective view of the implant simulating device of FIG. 2.

In the embodiment shown in FIGS. 3 and 4, implant simulating device 4 includes a base plate 27 and first and second arms 5 extending from base plate 27. Each of first and second arms 4 define a track 28. Cross members 6' slidingly engage track 28 to allow movement of cross member 6'. Each cross member 6' has a locking element 7 for fixing the position of cross member 6'.

As described in more detail below, because cross members 6' slidingly engage tracks 28 and fixation element simulators 3' are capable of angular positioning with respect to cross members 6', a correlation system 14 is used so that the position and orientation of fixation element simulators 3' are tailored to match that formed by fixation elements 3'. One manner of achieving the desired movement of cross member 6' is accomplished by forming cross member 6' as a top bar 6, a bottom bar 15, and a center piece 25 located therebetween. The ends of bottom bar 15 slide within tracks 28 so that cross members 6' slide within tracks 28 in a direction parallel to the length of base plate 27 and in a direction parallel to the width of base plate 27. A ball joint 10 is located in center piece 25 for receiving and allowing angular positioning of fixation element simulator 3'. Ball joint 10 has a threaded bore 10' that engages a threaded portion 16' of fixation element simulator 3' to allow height adjustment of fixation element simulator 3'.

After correlation of at least two fixation element simulators 3' to at least two implanted fixation elements 3, elongated element 2' can be inserted in openings 9 on heads 16 of fixation element simulators 3' to contour elongated element 2' to the implanted fixation elements 3 prior to implantation of elongated element 2'. Additionally, if cross members 6' are flexible, elongated element 2' can be bent to simulate changes in anatomy when elongated element 2' is deformed.

FIG. 3 shows correlation system 14 schematically as a position detecting system that includes at least one signal transmitter 11, at least one signal detector 12 for detecting the signals, and an analyzing unit 13 for processing the detected signals. Alternatively, signal transmitter 11 can be a reflector that reflects a signal from a separate signal transmitter to signal detector 12. As is well known in the art, the signals can be any electromagnetic or acoustical wave. For example, the position detecting system, like commercially available computer assisted surgical systems, can use light emitting diodes (LED's) for signal transmitters 11, at least one digital camera for signal detector 12, and image analyzing equipment. The position detecting system, like other computer assisted surgical system, can also operate with Hall sensors and at least one coil that produces a magnetic field in space. Position and orientation of either the Hall sensors or coils, and hence either the fixation elements 3 or fixation element simulators 3', are determined by processing the interference patterns.

In one embodiment, detectors 12 are associated with fixation element 3 and fixation element simulators 3' and transmitters 11 are located in the surrounding area at fixed spatial positions. As shown in FIG. 3, however, transmitters 11 can be associated with fixation element simulators 3' (and fixation elements 3) and detectors 12 are located in the surrounding area at fixed positions. In particular, transmitters 11 are located on an elongated inserter 8. It should be noted that transmitters 11 can be located directly on fixation elements 3 and fixation element simulators 3'. However, as elongated inserter 8 can be used to insert both fixation element 3 and fixation element simulators 3', by attaching transmitter 11 to inserter 8, the same transmitters are used to determine position and orientation of both fixation elements 3 and fixation element simulators 3'.

Figure 5:
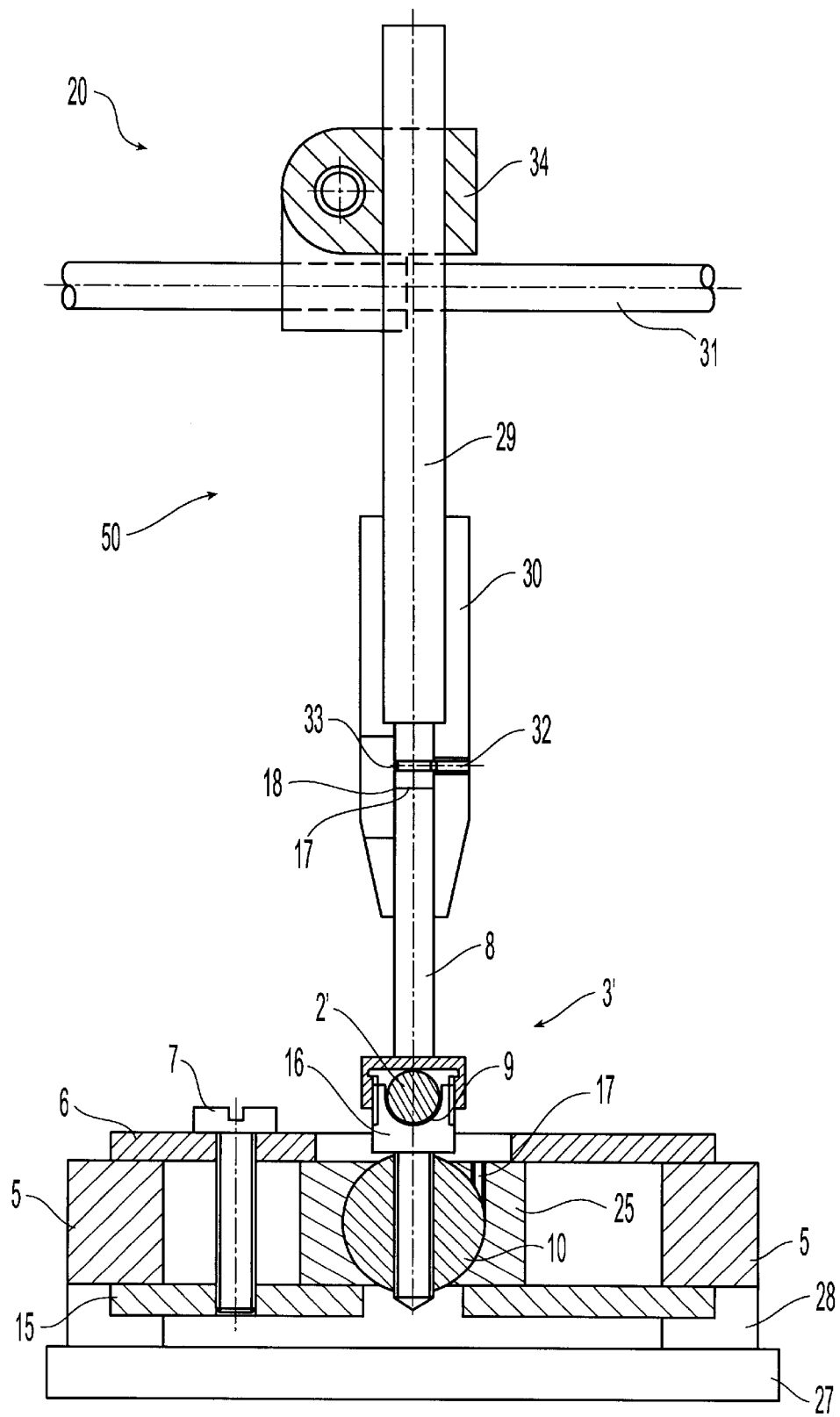
FIG. 5 shows a cross sectional view of the implant simulating device of FIG. 2 with the position detecting system replaced with a translation device.
Figure 6:
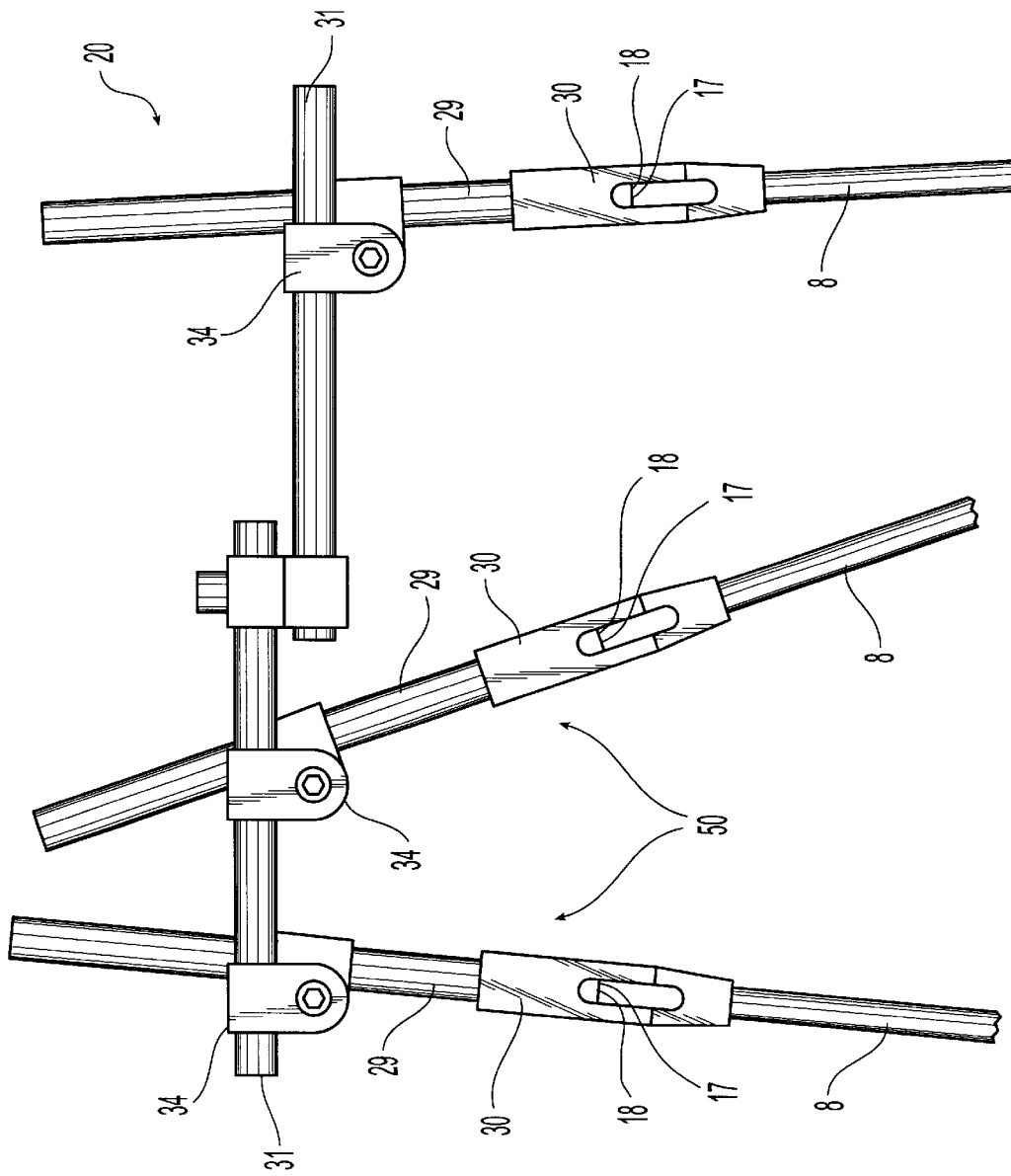
FIG. 6 shows a side view of the translation device of FIG. 5.

As an alternative to a position detecting system, correlation system 14 can be a mechanical based system, such as a pantograph, a scanning device, or some combination thereof, correlating at least two fixation element simulators 3' to at least two fixation elements 3. FIGS. 5 and 6 show an example of one such system. A translation device 20 allows transfer of the position and orientation of at least some of the fixation elements 3 to at least some of the fixation element simulators 3'. Translation device 20 includes a translator 50 for each of the fixation elements 3 whose position and orientation are to be transferred and a connecting rod 31 linking translators 50. Each translator 50 has a positioning pin 29 with a sleeve 30 for receiving at least a portion of elongated inserter 8 and a clamp 34 for coupling translator 50 to connecting rod 31.

In use, fixation elements 3 are implanted through percutaneous incisions with the assistance of elongated inserters 8. Translation device 20 is placed near elongated inserters 8 with each clamp 34 loosened to allow movement of the associated translator 50 until an end 18 of position pin 29 abuts an end of elongated inserter 8. As each translator 50 is brought into proper position, the associated clamp 34 is locked. After all clamps 34 are locked, sleeves 30 are uncoupled from elongated inserters 8 so that translation device 20 can be attached to elongated inserters 8 associated with fixation element simulators 3'. Because translators 50 each define a position and orientation of a fixation element 3, translation device 20 transfers position and orientation of fixation elements 3 to fixation element simulators 3'. Once fixation element simulators 3' mimic at least a portion of fixation system 1, elongated element 2 or elongated element 2' can be coupled to fixation element simulators 3' so that proper contouring is achieved prior to implantation.

Figure 7:
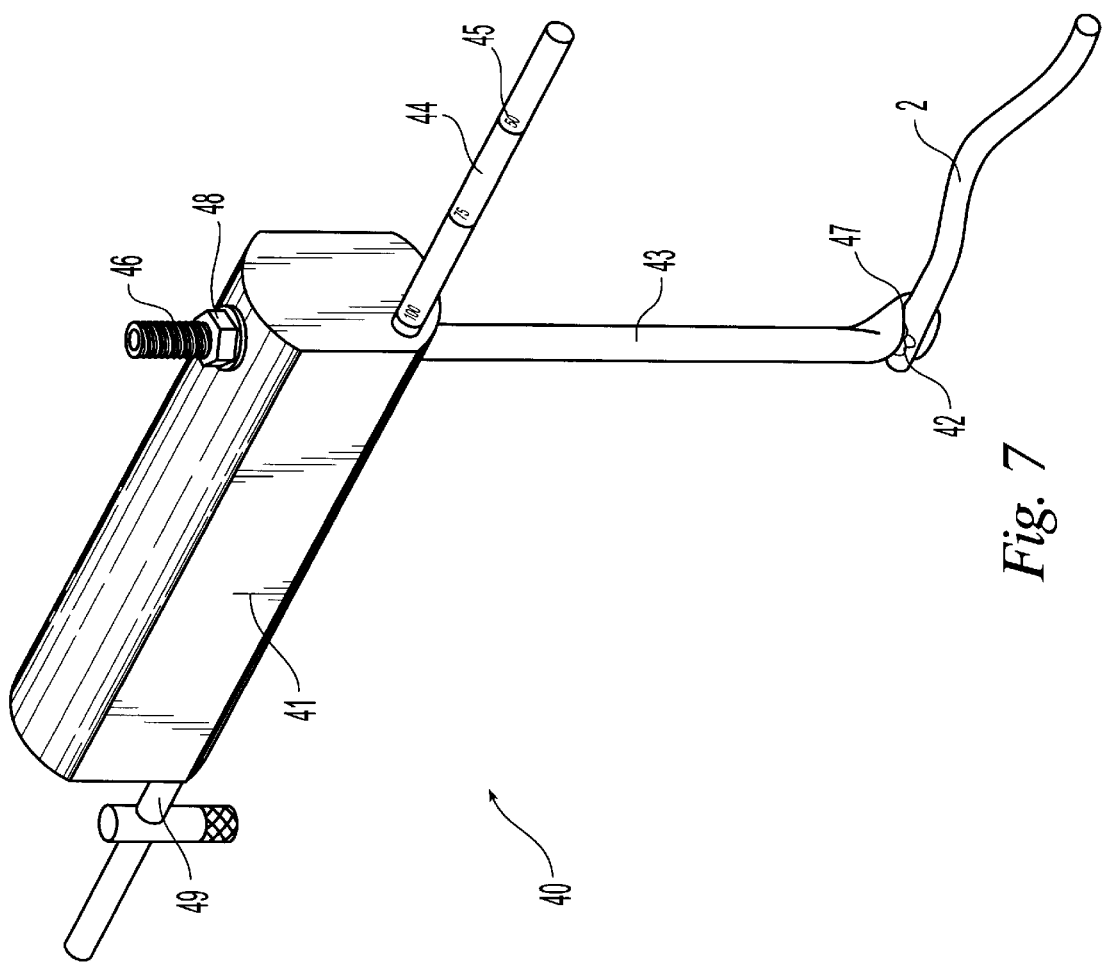
FIG. 7 shows a perspective view of a longitudinal element inserter according to the present invention.

FIG. 7 illustrates an elongated element inserter 40 for insertion of elongated element 2 through a small incision. Elongated element inserter 40 has a handle 41 with two perpendicular bores. An elongated holder 43 with a recess 47 for holding elongated element 2 extends through the first bore. Elongated holder 43 has a hollow shaft so that a locking pin 42 extends through the shaft for securing elongated element 2 in recess 47. Elongated holder 43 can be fixedly secured in handle 41 such that when elongated element is inserted in recess 47, it may assume a certain orientation with respect to its longitudinal axis. The length of elongated holder 43 is such that elongated element 2 can be inserted beneath the skin or muscles, while handle 41 remains outside the body.

A position and orientation display 44 having a length scale 45 extends through the second bore. Display 44 is parallel to elongated element 2 secured in recess 47. With the help of position and orientation display 44, it is possible to detect the position and orientation of elongated element 2 beneath the skin or muscles for adaptation or implantation. Elongated element 2 can be aligned parallel to position and orientation display 44 by adjusting nut 48 and elongated holder 43. The length of position and orientation display 44 can be aligned by adjusting screw 49.

The advantages achieved through the present invention include, but are not limited to the following:

A) The soft tissue need not be opened to determine the contours of the required elongated element.

B) A trial rod or bending template is not introduced deep into the implant and removed again with any hindrance by the soft tissue, so there is no risk of the trial rod or the bending template being deformed. The trial rod or the bending template can be simply inserted into the device according to the present invention and removed again as needed without being deformed.

C) The device according to the present invention also facilitates checking on whether the elongated element has been pre-bent correctly.

D) Any correction that might be necessary can be simulated by bending the elongated element itself.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An implant simulating device for simulating position and orientation of an elongated element with respect to a plurality of fixation elements of a fixation system, the implant simulating device comprising:

a base plate having a length and a width;

first and second arms extending from the base plate, each of the first and second arms defining a track;

at least two cross members, each cross member configured and dimensioned for slidingly engaging the track of the first and second arms and having a locking element for fixing the position of the cross member;

a fixation element simulator associated with each of the at least two cross members and capable of angular positioning with respect to the cross members; and a correlation system for correlating at least two fixation element simulators to at least two fixation elements of the fixation system, wherein coupling of an elongated element in the at least two fixation element simulators after correlation by the correlating system allows the elongated element to be configured and dimensioned for coupling to the fixation elements prior to implantation.

2. The implant simulating device of claim 1 wherein each cross member includes a ball joint for receiving and positioning the fixation element simulator.

3. The implant simulating device of claim 2 wherein each cross member comprises top and bottom bars and a center piece located therebetween and wherein the ball joint is located in the center piece and wherein the ends of the bottom bar slide within the track of the first and second arms so that each cross member is slidable in a direction parallel to the length of the base plate and in a direction parallel to the width of the base plate.

4. The implant simulating device of claim 2 wherein the fixation element simulators include a threaded portion and each ball joint includes a threaded bore for engaging the threaded portion of the fixation element simulator to allow height adjustment of the fixation element simulator.

5. The implant simulating device of claim 1 wherein the elongated element is bent to conform to the fixation element simulators and each cross member is flexible to simulate changes in anatomy when the bent elongated element is deformed.

6. The implant simulating device of claim 5 wherein the bent elongated element is coupled to the fixation elements.

7. The implant simulating device of claim 1 wherein the elongated element is used as a template for bending a second elongated element.

8. The implant simulating device of claim 1 wherein the correlation system is a position detecting system comprising:
   at least one signal transmitter;
   at least one sensor for detecting the signal(s); and
   an analyzing unit for processing the signal(s) to determine position and orientation of at least some of the fixation elements.

9. The implant simulating device of claim 8 wherein a signal transmitter is associated with each fixation element.

10. The implant simulating device of claim 9 wherein each transmitter is located on an elongated inserter which is associated with a fixation element.

11. The implant simulating device of claim 10 wherein the elongated inserter is configured and dimensioned to mate with a fixation element simulator.

12. The implant simulating device of claim 9 wherein each signal transmitter comprises at least one light emitting diode (LED) and the sensor comprises a digital camera.

13. The implant simulating device of claim 8 wherein the signal comprises an electromagnetic or acoustic wave.

14. The implant simulating device of claim 1 wherein the correlation system comprises a pantograph, a scanning device, or a combination thereof.

15. The implant simulating device of claim 1 wherein the correlation system is a translation device for transferring position and orientation of at least some of the plurality of fixation elements, the translation device comprising at least two translators and a connecting rod linking the at least two translators, each of the at least two translators comprising:
   a positioning pin having first and second ends;
   a sleeve having first and second ends, the first end configured and dimensioned for receiving the first end of the positioning pin and the second end configured and dimensioned for receiving at least a portion of an elongated inserter coupled to a fixation element; and
   a clamp having a first portion coupled to the connecting rod and a second portion coupled to the second end of the positioning pin, the first portion rotatable with respect to the second portion for adjusting position and orientation of the positioning pin to align the translator with one of the plurality of fixation elements,
   wherein transferring each of the at least two translators to one of the at least two fixation element simulators results in the implant simulating device mimicking at least a portion of the fixation system.

16. The implant simulating device of claim 1 further comprising an elongated element inserter comprising:
   a handle;
   an elongated holder extending from the handle in a first direction and having a hollow shaft with a recess on a distal end for receiving a portion of the elongated element;
   a locking pin insertable in the hollow shaft of the holder for securing the longitudinal element in the recess; and
   a position and orientation display extending from the handle in a second direction and having a length scale,
   wherein the position and orientation display is parallel to the portion of the elongated element.

17. A method for pre-bending an elongated element of a fixation system including at least two fixation elements for connecting the elongated element to bone, the method comprising the steps of:
   mounting an elongated inserter on each of at least two of the fixation elements, the fixation elements collectively defining a desired shape;
   transferring position and orientation of at least two of the fixation elements to at least two fixation element simulators to thereby mimic the desired shape; and
   bending the elongated element to have a configuration that matches the desired shape.

* * * * *